US007524509B2

(12) United States Patent
Burt et al.

(10) Patent No.: US 7,524,509 B2
(45) Date of Patent: Apr. 28, 2009

(54) PROTEOSOME-LIPOSACCHARIDE VACCINE ADJUVANT

(75) Inventors: David S. Burt, Dollard-des-Ormeaux (CA); George H. Lowell, Hampstead (CA); Gregory L. White, Montreal (CA); David Jones, Baie D'Urfe (CA); Clement Rioux, Ile Bizard (CA)

(73) Assignee: ID Biomedical Corporation of Quebec, Laval (CA)

( * ) Notice: Subject to any disclaimer, the term of this patent is extended or adjusted under 35 U.S.C. 154(b) by 0 days.

(21) Appl. No.: 10/094,424

(22) Filed: Mar. 11, 2002

(65) Prior Publication Data

US 2003/0044425 A1 Mar. 6, 2003

(51) Int. Cl.
*A16K 39/02* (2006.01)
*A16K 39/095* (2006.01)
*A16K 39/116* (2006.01)
*A16K 39/385* (2006.01)
*A16K 47/00* (2006.01)
*A16K 45/00* (2006.01)

(52) U.S. Cl. .............. 424/234.1; 424/249.1; 424/250.1; 424/203.1; 424/197.11; 424/193.1; 424/278.1; 424/282.1

(58) Field of Classification Search .............. 424/184.1, 424/192.1, 193.1, 194.1, 202.1, 250.1, 774, 424/803, 804
See application file for complete search history.

(56) References Cited

U.S. PATENT DOCUMENTS 6,803,042 B2 * 10/2004 Lowell .................... 424/250.1

FOREIGN PATENT DOCUMENTS

| WO | WO94/20070 | 9/1994 |
| WO | WO 95/11008 | 4/1995 |
| WO | WO98/01558 | 1/1998 |
| WO | WO98/20734 | 5/1998 |
| WO | WO00/36107 | 6/2000 |

OTHER PUBLICATIONS

Orr et al, Infection and Immunity, Jun. 1993, p. 2390-2395, Vo. 61, No. 6.*
Kraft et al, International Archives of Allergy Immunology, 1999:118:171-176.*
Mallet et al (Infection and Immunity, Jun. 1995, p. 2382-2386).*
Slowe et al (Immunology, 1975, Nov. 29(5):825-34).*
Kraft et al (International Archives of Allergy Immunology, 1999;118: 171-176).*
Wiedermann et al (Clin. Exp. Immunol 1998:111:144-151, p. 144-151).*
Berstad et al., "Inactivated Meningococci and Pertussis Bacteria are Immunogenic and act as Mucosal Adjuvants for a Nasal Inactivated Influenza Virus Vaccine," *Vaccine, Butterworth Scientific Guildford* 18 (18):1910-1919, Mar. 2000.
Ben-Yedidia et al., "Synthetic Peptide-based Vaccines against Influenza," *Letters in Peptide Science 5* : 341-344, 1998.
Drabick et al., "Safety and Immunogenicity Testing of an Intranasal Group B Meningococcal Native Outer Membrane Vesicle Vaccine in Healthy Volunteers," *Vaccine, Butterworth Scientific, Guildford* 18(1-2):160-172, Aug. 1999.
Levi et al., "Intranasal Immunization of Mice against Influenza with Synthetic Peptides Anchored to Proteosomes," *Vaccine* (13):1353-1359, 1995.
Lowell et al., "Proteosome-Lipopeptide Vaccines: Enchancement of Immunogenicity for Malaria CS Peptides," *Science 240*:800-802, May 6, 1998.
Mallett et al., "Immunogenicity of a Proteosome-Plesiomonas Shigelloides LPS Vaccine for *Shigella sonnei* in Adult Volunteers," *Abstracts of the General Meeting of the American Society for Microbiology 97*:258, May 1997.
Orr et al., "Enhancement of Anti-Shigella Lipopolysaccharide (LPS) Response by Addition of the Cholera Toxin B Subunit to Oral and Intranasal Proteosome-Shigella Flexneri 2A LPS Vaccines," *Infection and Immunity, American Society for Microbiology 62*(11):5198-5200, Nov. 1994.
Orr et al., "Development of Bivalent Shigella Flexneri 2a/Shigella Sonnei Vaccine Composed of LPS-Propteosome Hydrophobic Complex," *Abstracts of the Interscience Conference on Antimicrobial Agents and Chemotherapy 35*:159, Sep. 1995.
Rinji Kwana ed., "Hyojun Biseibutsugaku (Standard Microbiology)", *6th edition, Igaku-Shoin Ltd.*, pp. 113-114, 1997.
Ruegg et al., "Preparation of Proteosome-Based Vaccines Correlation of Immunogenicity with Physical Characteristics," *Journal of Immunological Methods 135*(1/2):101-109, 1990.
Slavik et al., "The Complex Formation of Influenza Virus Envelope Glycoproteins with Outer Membrane Proteins of Neisseria Meningitidis or Borrelia Burgdorferi," *Acta Virologica 37*:449-458, 1993.

* cited by examiner

*Primary Examiner*—Robert Mondesi
*Assistant Examiner*—Vanessa I. Ford
(74) *Attorney, Agent, or Firm*—Seed IP Law Group PLLC

(57) ABSTRACT

An adjuvant complex composed of bacterial outer membrane protein proteosomes complexed to bacterial liposaccharide is prepared to contain the component parts under a variety of conditions. The complex can be formulated with antigenic material to form immunogenic compositions, vaccines and immunotherapeutics. An induced immune response includes protective antibodies and/or type 1 cytokines is shown for a variety of protocols.

20 Claims, 8 Drawing Sheets

Manufacture of S. flexneri 2a LPS: FLOW CHART 2

Fig. 2

```
Production seed S. flex. BS 103 into
3 X 1L shaker flasks of
trypticase soy broth suppl. with
glucose and MgSO₄
Incubated at 37° C X 16 - 24 hours
           ↓
300 L fermentation, trypticase soy broth suppl.
with glucose and MgSO₄
250 rpm agit.*, 37° C, pH 7.5,
300 L/min. O₂
           ↓  ← Fermentation to stationary
                by OD₆₀₀ (9 -10 hours)
Cool to 10° C, harvest in
continuous feed centrifuge
           ↓
Rehydrate paste X 1 hour at R.T.
in 3 mL of 0.9 M NaCl, 0.005 M EDTA and 10
mg lysozyme per g paste
           ↓
Add DNase to 50 u/mL and MgCl₂
To 0.025M, inc. 30 min. at R.T.
           ↓
Homogenize in microfluidizer,
14,000 to 19,000 psi
           ↓
Fresh DNase to 50 u/mL inc. 30 min. at R.T
           ↓
Heat to 68° C, add = vol. 90% phenol
Incubate 68° C x 30 min., shaking
           ↓
Cfg. at 4° C, harvest aqueous phase
           ↓  → Reserve aqueous phase
Repeat extraction of phenol phase x 2
with WFI at 68° C,
pool all aqueous phase materials
           ↓  → Discard phenol phase
Add EtOH to 15%, CaCl₂ to 10mM
Inc. 1 hr. at R.T., cfg. 10,000 X G
           ↓  → Discard pellet
Concentrate, diafilter on 10,000 MW membrane
into 0.15 M NaCl, 0.05 M Tris, 0.01 M EDTA,
0.1% Empigen, pH 8.0
           ↓
0.22 µm aseptic filtration  →  LPS BULK, store -80° C
```

* agitation rate varied to maintain dissolved $O_2 \geq 25\%$

Figure 4 a) and b) show the levels of specific serum IgG (a) and lung lavage IgA (b) elicited when a constant amount of HA was mixed with different amounts of IVX-908 and used to immunize mice intranasally.

a)

b)

Figure 4 c) and d) show the levels of specific serum IgG (c) and lung lavage IgA (d) elicited when a constant amount of IVX-908 (either 1 or 0.3 μg) was mixed with different amounts of HA and used to immunize mice intranasally.

c)

d)

Figure 5 a) shows the numbers of immunized (n=10) or control (n=9) mice surviving challenge with a live, mouse-adapted, homotypic variant influenza virus. Figure 5 b) shows mean weight loss (a measure of morbidity associated with infection by influenza virus) in the survivors in each group. Error bars indicate standard errors on the mean.

a)

b)

Figure 6 shows specific antibody responses in serum of mice immunized i.n. or i.m. with Ovalbumin with or without IVX-908. Titers are expressed as geometric mean concentrations of specific IgG (□g/ml) with 95% confidence limits indicated by error bars.

PROTEOSOME-LIPOSACCHARIDE VACCINE ADJUVANT

FIELD OF INVENTION

This invention relates to adjuvants for enhancing the immunogenicity and improvement of the immune response of antigens and to methods and compositions for preparing and using them.

BACKGROUND OF THE INVENTION

The ability of antigens to induce protective immune responses in a host can be enhanced by combining the antigen with immunostimulants or adjuvants. Alum-based adjuvants are almost exclusively used for licensed injectable human vaccines, however, while alum enhances certain types of serum antibody responses (Type 2), it is poor at enhancing other types of antibody responses (Type 1) and is a poor activator of cellular immune responses that are important for protection against intracellular pathogens and for therapeutic vaccines for cancer and allergy. Furthermore, alum enhances allergic reactions due to production of IgE. Although numerous substances have been tested and shown to be potent adjuvants for antibody and cellular (Type 1) immune responses in animal models, very few have proved to be suitable for use in humans due to unacceptable levels of reactogenicity and/or disappointing immuno-enhancing abilities. Furthermore, there are currently no licensed adjuvants capable of enhancing immune responses at mucosal surfaces where the majority of infectious agents enter the host. Indeed, development of the most promising nasally delivered mucosal adjuvants, the bacterial enterotoxins (e.g. mutated cholera and heat-labile toxins), have been halted in North America due to their ability to be transported to, and cause inflammation in the olfactory bulb region of the CNS of rodents. There is a need for potent adjuvants that are safe in humans and capable of inducing protective systemic and mucosal humoral and cellular immune responses.

Lipopolysaccharides (LPS) from gram negative bacteria are potent adjuvants. LPS activates the innate immune system causing production of inflammatory cytokines such as IL-1, TNF-$\square$, IL-10 and IL-12 from macrophages and dendritic cells; IL-1, IL-6 and IL-8 from endothelial cells and IL-8 from epithelial cells. In addition, LPS is a B cell activator in mice and, to a certain extent in humans, as evidenced by B cell mitogenicity and stimulation of polyclonal antibody secretion. LPS mediates it's effects by binding to CD14 molecules and activation of toll like receptors (TLR) on the surface of antigen presenting cells leading to the initiation of a transcriptional cascade, gene expression and secretion of pro-inflammatory molecules.

Despite the adjuvant potential of LPS, its use in humans has been restricted due to the associated endotoxicity mediated by the lipid A portion of the molecule. Chemical modification of the lipid A region of LPS was shown to substantially detoxify lipid A (e.g. monophosphoryl lipid A or MPL-A or e.g. alkali-detoxification to remove certain fatty acids) while maintaining certain adjuvant properties (see Qureshi et. al. J. Biol Chem 1982; 257:11808-15). While MPL-A exhibited potent adjuvant activity in animals, the experience in humans has been inconsistent, showing poor adjuvant activity with some antigens and unacceptable reactogenicity overall in many situations.

Non-covalent proteosome-LPS complexes, containing proteosomes from Neisseria meningitidis and purified LPS from *Shigella flexneri* or *Plesiomonas shigelloides*, have been administered to humans intranasally and orally in phase 1 and phase 2 clinical trials in the context of stand-alone vaccines. These vaccines induce protective immune responses against *Shigella flexneri* or *S. sonnei* infection, respectively, in animals (Mallet et. al. Infect and Immun 1995; 63:2382-86) and humans (Fries et. al. Infect Immun. 2001; 69:4545-53) when given via the intranasal route. Further, these complexes were well-tolerated via the nasal or oral routes in humans at very high doses (up to 1.5 mg of proteosomes along with comparable amounts of LPS given intranasally and up to 2 mg of each of the proteosome and LPS components given orally) (Fries et. al. 2000) and showed no olfactory bulb or other CNS associated toxicity in small animal toxicity studies. Proteosomes consist predominantly of porin proteins and other outer membrane proteins. Evidence suggests that proteosome porins may also induce IL-12 from dendritic cells and induction of CD8+ T cells (Jeannin et. al. Nature Immunology 2000; 1:502-509) and activation of Hela cells to produce IL-8 (Pridmore et. al. J. Infect Dis 2000; 10:183). Proteosome porins also upregulate B7.2 (CD28) co-stimulatory molecules on antigen presenting cells via the activation of the toll-like receptor 2 (Massari et. al. J. Immunol. 2002, 168: 1533-1537).

Dalseg et. al. (in *Vaccines* 96 pp. 177-182 (Cold Spring Harbor laboratory Press, 1996)) report the use of meningococcal outer membrane vesicles (OMV's) as a mucosal adjuvant for inactivated whole influenza virus. Dalseg and his associates and collaborators have reported that the OMV's they prepare employ a process that retains 6% to 9% of endogenous lipooligosaccharide (LOS) remaining compared to the amount of total OMV protein by weight. These OMV preparations have also been reported to specifically retain 16% of detergent (deoxycholate) in their OMV's, an amount that may be unhealthy or toxic in toxicity studies or in humans.

BRIEF DESCRIPTION OF INVENTION

The instant invention (IVX-908) describes compositions of and processes for production of novel formulations that are adjuvants for antigens and result in adjuvanted vaccines or immunotherapeutics when the invention and antigen(s) are combined by simple mixing and the adjuvanted vaccines or immunotherapeutics are delivered by a parenteral or mucosal route. The adjuvant consists of two major components. The first component is an outer membrane protein preparation of proteosomes prepared from gram-negative bacteria including, but not limited to Neisseria meningitidis. The second component is a preparation of liposaccharide. Liposaccharide includes native or modified lipopolysaccharide (LPS) and lipooligosaccharide derived from *S. flexneri* or *Plesiomonas shigelloides* or other gram-negative bacteria including, but not limited to, *Shigella, Plesiomonas, Escherichia* or *Salmonella* species. The two components may be formulated at specific initial ratios by processes described, so as to optimize interaction between the components resulting in stable non-covalent complexes of the components to each other. The processes generally involve the mixing of the components in a selected detergent solution (e.g. Empigen BB, Triton X-100, and/or Mega-10) and then effecting complexing of the components while removing detergent by dialysis or, preferably, by diafiltration/ultrafiltration methodologies. Mixing, co-precipitation and/or lyophilization of the two components may also be used to effect adequate complexing or association.

The end result of the process is the production of an adjuvant that when administered together with antigens forms an adjuvanted vaccine or immunotherapeutic that can be delivered by a mucosal route (such as nasal, oral, oropharyngeal, ocular, genitourinary mucosal including vaginal, sublingual, intrapulmonary, intratracheal or rectal) or a parenteral route (such as intramuscular, subcutaneous, intravenous, intraperitoneal, submucosal, intradermal) or a transdermal, topical or transmucosal route to induce enhanced levels of serum and/or mucosal antibodies and/or type 1 cellular immune responses against the antigen compared with the antigen alone given by the same routes. In the following examples, mixtures containing proteosome-LPS (using LPS from either *Shigella* or *Plesiomonas* or *Escherichia* or *Salmonella*) and a mono or multivalent split or purified recombinant influenza antigen and delivered by liquid or spray or by injection as an adjuvanted influenza vaccine induced specific anti-influenza immune responses including, for example one or more of the following: a) serum IgG antibodies or serum antibodies measured in functional assays including, but not limited to, hemagglutination inhibition (HAI) antibodies; it is noted that HAI responses are significant since their induction is known to correlate with protection against influenza in humans; b) mucosal antibodies including IgA in mucosal secretions collected from the respiratory, gastrointestinal or genitourinary tracts including, but not limited to the nasopharynx, lungs and vagina and c) correlates of cell-mediated immunity (CMI) including the switch or decrease from higher or predominant type 2 responses to result in mixed, balanced, increased or predominant type 1 responses, for example, as measured by the induction of cytokines such as IFN-γ without comparable increases in induction of certain type 2 cytokines such as IL-5 whose levels may, for example, be maintained, decreased, or absent. Such Type 1 responses are predictive of the induction of other CMI associated responses such as development of cytotoxic T cells (CTLs) indicative of Th1 immunity.

The ability of the adjuvant given nasally or intramuscularly to elicit these three types of responses against the antigen indicate that the vaccine can provide immunity against infectious diseases since functional serum antibodies (including HAI antibodies) and virus specific lung antibodies are generated. Also, the induction of vaginal IgA for mucosally administered adjuvanted vaccines using the adjuvant of the instant invention supports utilization against mucosal infections or allergies distal from the site of immunization such as at the gastrointestinal or genitourinary tracts. Furthermore, the induction of type 1 of responses assists the elimination of residual or intracellular virus, parasite or certain bacterial pathogens. In addition the ability of the adjuvant to produce type 1 immune responses against the antigen will be beneficial for producing effective therapeutic vaccines for example against cancer, autoimmune diseases and allergy where CTL and Th1 cytokine responses are important.

For example, allergic rhinitis can often be effectively controlled by immunotherapy —a series of injections with increasing doses of the substance against which the individual is allergic. Allergic rhinitis can be cured in approximately 50% of individuals who undergo classic immunotherapy. Successful immunotherapy is associated with one or more of the following: a switch from T cell responses that result in the production of type 2 cytokines (e.g. IL-5 and IL-4) to those that produce type 1 cytokines (e.g. IFN-γ) and/or an increase in IgG and/or reduction in IgE specific for the allergen. However, in order to achieve these results, up to three years of repeated immunizations are required. The use of allergens together with adjuvants that promote type 1 immune responses may enhance the effectiveness of such immunotherapy and reduce the number of immunizations required.

In the following example we show the results of studies in mice immunized intranasally with IVX-908 together with rBet v 1a as a recombinant protein representing the major allergen of Birch tree pollen or Birch tree pollen extract. The results for both the recombinant protein and allergen extract demonstrate that IVX-908 converts T cell cytokine production against Bet v 1a from a type 2 to a predominately type 1 phenotype. Furthermore, the type 1 response is associated with the increased production of allergen-specific serum IgG compared with the allergen alone, and a reduction in Bet v 1a-specfic serum IgE compared with allergen administered with aluminum phosphate, a depot and Type 2 adjuvant known to sensitize mice for allergic responses against an allergen. Importantly, the increase in the type 1 cytokine, IFN γ was also observed following the immunization of allergic mice with the same allergen given with IVX-908. The pre-allergic state of the mice mimics the situation in allergic humans, suggesting that IVX-908/allergen formulations may be candidates for therapeutic allergy vaccines.

It is noted that the instant invention can readily adjuvant vaccines containing single, monovalent or multi-component antigens such as peptides, proteins, toxoids, glycoproteins, glycolipids, carbohydrates and/or polysaccharides, isolated from biologic organisms of the animal or plant kingdom that may be infectious organisms, such as parasites, viruses and bacteria, or may be extracts or purified or chemically modified extracts of allergens derived from unicellular or multicellular organisms or may be chemical material. It is also envisioned that whole or disrupted microorganisms including viruses, bacteria or parasites, attenuated or inactivated could be used as antigen. These materials may also be produced by synthetic or recombinant molecular procedures to induce immunity to and protect against several strains of a particular organism or multiple organisms or disease-causing agents or against allergies, cancer or auto-immune diseases. The utility in human and veterinary fields is proposed. Furthermore, the invention can be used to enhance immunity when given together with the antigen as an adjuvanted vaccine or immunotherapeutic as priming or boosting immunizations prior to or subsequent to administering the antigen (by mucosal or parenteral routes) without the instant invention.

For parenteral, nasal, oral or suppository use, the adjuvant may be given together with amounts of a variety of excipients or other adjuvants including oils, emulsions, nano-emulsions, fats, waxes, buffers, or sugars, as diluents or vehicles customary in the art to provide stable delivery of the product in the desired delivery format.

Of particular note, it is emphasised that using the instant invention as an adjuvant is particularly novel since it may, in a preferred embodiment, combine the adjuvant effect of proteosomes together with the immunostimulatory potential of LPS. This complex would not have been predicted to be effective from prior art since it contains full-length LPS that is normally toxic when given alone. As a stable proteosome complex LPS is non-toxic by the nasal and parenteral routes in the given examples as verified by both pre-clinical safety, immunogenicity and toxicity as well as in clinical studies in FDA-approved phase I and phase II clinical trials.

The instant invention may be composed of purified or recombinant bacterial outer-membrane proteins from gram-negative bacteria species including but not limited to *Neisseria meningitidis* strains. The LPS can be derived from gram negative bacteria such as, but not limited to *Shigella* or *Plesiomonas* or *Escherichia* or a *salmonella* species and can be from the same or different species of the bacteria used to provide the outer membrane protein proteosomes. In the preferred embodiment the final liposaccharide or LPS content by weight as a percentage of the total proteosome protein can be between about 13% and 300% and, depending on the specificity of the application and route of administration may be effective and practical for use at liposaccharide or LPS percentages of 20% to 200%, or may be further distinguished in a particular application at a liposaccharide percentage of between 30% to 150%. The instant invention together with antigen is designed to deliver adjuvanted vaccines by mucosal (nasal, sub-lingual, oral or rectal) or parenteral (intramuscular, subcutaneous, intradermal or transdermal) routes for use in the prevention or treatment of cancer, autoimmune, viral or microbial diseases or against certain toxins or biologic threat agents or allergies whether acquired by mucosal routes such as and specially by inhalation, or by ingestion or sexual transmission, or by parenteral routes such as transdermal, intradermal or subcutaneous or intramuscular.

An embodiment of the instant invention is a process for preparing proteosomes with endogenous lipooligosaccharide (LOS) content of between 0.5% up to about 5% of total protein. Another embodiment of the instant invention specifies a process for preparing proteosomes with endogenous liposaccharide of between about 12% to about 25%, and in a preferred embodiment, between 15% and 20% of total protein.

The instant invention specifies a composition containing liposaccharide derived from any gram negative bacterial species which may preferably be naturally or recombinantly different from or the same as the gram negative bacterial species which is the source of the proteins in the invention. The composition of the present invention may be optimised, specifically specified by the formulators and varied at will to contain amounts of proteosomes and liposaccharide such that the resultant composition of the instant invention contains liposaccharide to an amount that is at least about 13% by weight of the weight of total proteosome protein and in a preferred embodiment, may be from 15% to 300% and may be further preferred, depending on the application, to be between 20% to 200% of the total protein on a weight:weight basis or even between 30% and 150% of the total protein.

A most preferred embodiment of the instant invention is the adjuvant composition wherein the proteosomes are prepared from Neisseria meningitides and the liposaccharide is prepared from *Shigella flexneri* or *Plesiomonas shigelloides* and the final liposaccharide content is between 50% to 150% of the total proteosome protein by weight.

BRIEF DESCRIPTION OF THE FIGURES

FIG. 2 shows a scheme for the manufacture of *S. flexneri* 2a LPS (Flow Chart 2).

FIG. 5*b*) shows mean weight loss (a measure of morbidity associated with infection by influenza virus) in the survivors in each group. Error bars indicate standard errors on the mean.

DETAILED DESCRIPTION OF THE INVENTION

Figure 1A:
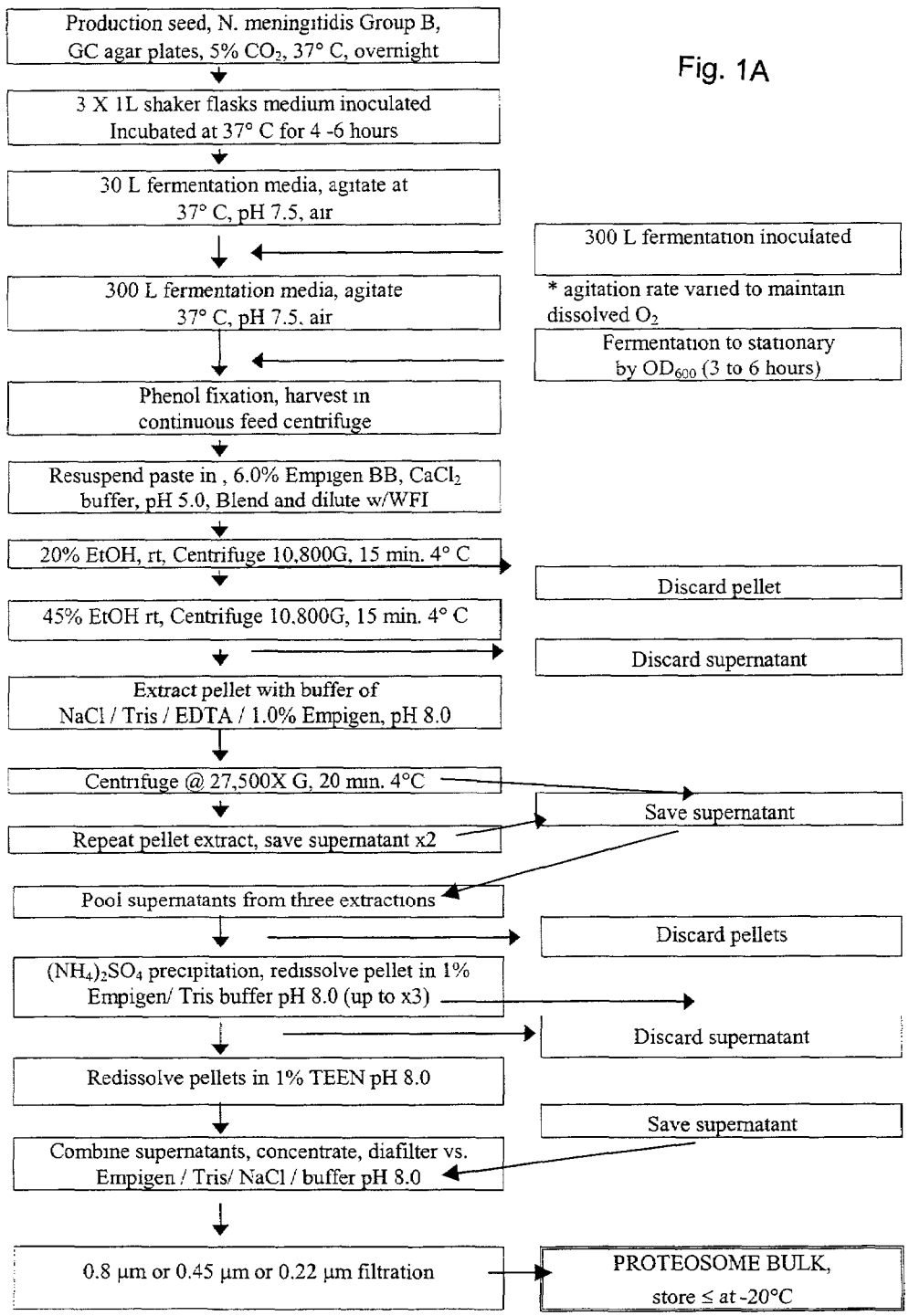
FIG. 1A and B show, respectively two embodiments for the manufacture of proteosome bulk material (Flow Chart 1A and Flow Chart 1B).

Results show the following activities of IVX-908 adjuvant when mixed with recombinant and split antigens from influenza virus:

A. By the Injectable Route:
1. Induces up to eight-fold increases in serum HAI and IgG compared with injectable split flu influenza vaccine alone
2. Shifts elicited immune responses to Type 1 (CMI) responses compared to split flu influenza vaccine alone B. By the Nasal Route:
1. Induces>100-fold increases in serum HAI and IgG responses, compared with split flu influenza antigen alone given by the nasal route
2. Induces up to 10-fold higher specific serum HAI and IgG compared with split flu given by injection
3. Induces>100-1000 fold higher specific IgA in lung and/or nose compared with split flu influenza antigen alone given nasally or by injection
4. Induces up to 160-fold higher specific IgA in genital tract compared with split flu influenza antigen alone given nasally or by injection
5. Shift to Type 1 (CMI) responses compared to split flu alone
6. Amounts of IVX-908 as little as 0.3 ug to 1ug are sufficient to achieve optimal enhancement of serum IgG responses against split-flu HA
7. Recombinant influenza HA co-administered with IVX-908, induces responses which are protective against mortality and morbidity, and superior to those induced by injection or i.n. administration of the antigen alone
8. IVX-908 prepared at protein:LPS ratios of 3:1 to 1:3 using LPS from *Shigella, Escherichia* and *Salmonella* species were effective.

The results show that respiratory or parenteral immunization with the instant invention and influenza split flu antigen induces enhanced specific anti-influenza HA antibody formation in each of the serum and mucosal bio-samples compared to immunizing with the influenza split product without adjuvant.

Results show the following activities of IVX-908 adjuvant when mixed with rBet v 1a, the major allergen from Birch pollen as either recombinant allergen or Birch pollen allergen extract and administered via the nasal route.

1. The nasal IVX-908 and rBet v 1a mixture enhanced induction of the type 1 cytokine, IFN-γ by 50- and 74-fold compared with Bet v 1a alone and Bet v 1 a formulated in aluminium phosphate respectively. The nasal IVX-908 and Birch pollen extract (BPEx) mixture enhanced induction of the type 1 cytokine, IFN-γ, by >44- and 3-fold compared with Bet v 1a alone and Bet v 1a formulated in aluminium phosphate respectively.
2. The increases in IFN-□ production by the IVX-908/Bet v 1a and IVX-908/BPEx mixtures were not associated with an increase in IL-5 secretion, indicating that IVX-908 directed the immune response against Bet v 1a towards a type 1-biased T cell response.

3. Serum IgE induced by the IVX-908 Bet v 1a and IVX-908/BPEx mixtures were approximately 37- and 44-fold lower than that induced by the allergens given with aluminium phosphate respectively.
4. Allergen-specific serum IgG was increased by >400-fold and 22-fold for mice immunized with the IVX-908/Bet v 1a and IVX-908/BPEx mixtures compared with Bet v 1a and BPEx alone, respectively.
5. In mice sensitized with Bet v 1a plus alum, the production of the type 1 cytokine, IFN-γ was increased by 4.7- and 33-fold following immunization with IVX-908/rBet v 1a and IVX-908/BPEx respectively compared with the corresponding allergens alone. In these mice, the levels of the type 2 cytokine, IL-5 were reduced compared to the corresponding allergens alone.
6. In mice immunized nasally with IVX-908/allergen mixtures and subsequently given a sensitizing injection with Bet v 1a plus alum the type 1 cytokine, IFN-γ increased by 10-fold compared with birch pollen extract alone. In these mice, the levels of the type 2 cytokine, IL-5, were not similarly elevated and indeed were somewhat reduced compared to birch pollen extract alone.

The results demonstrate that IVX-908/allergen formulations induce strong type 1 cytokine responses in allergen naive and sensitized mice, suggesting that these formulations prepared with purified or recombinant proteins or extracts of allergens may be used as vaccines or therapeutics for specific immunotherapy for allergic diseases. Results show the following activities of IVX-908 adjuvant when mixed with ovalbumin (OVA), a known poor immunogen and given by the nasal or injectable route.

1. Enhances OVA-specific serum IgG titers by greater than 60- and 75-fold via the nasal and injectable routes respectively compared with antigen alone,
2. Enhances the secretion of OVA-specific IFN-γ and IL-5 from re-stimulated splenocytes compared with antigen alone resulting in a balanced type of immune response.

EXAMPLES

Example 1

Production of Proteosomes

Figure 1B:
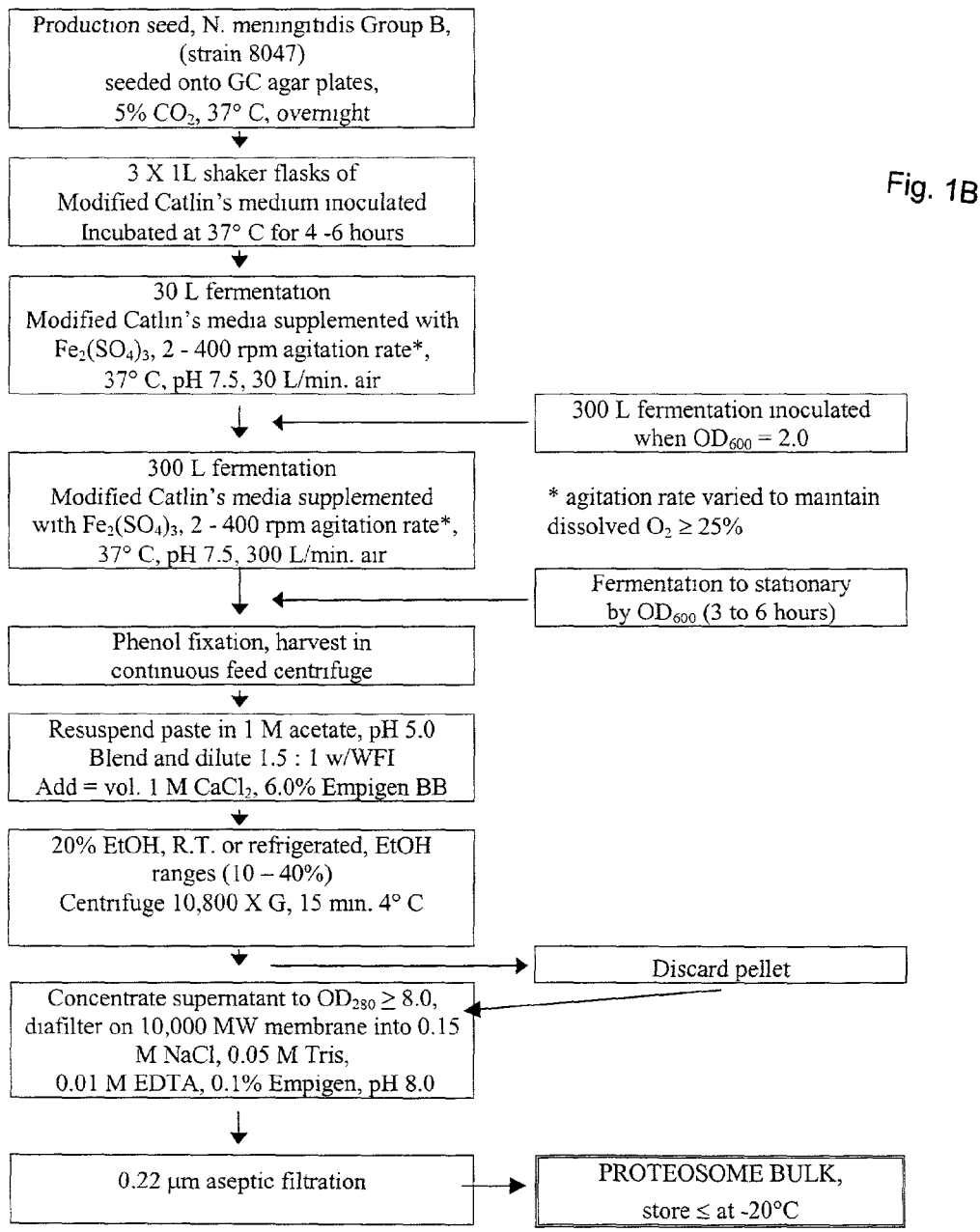
Figure 3:
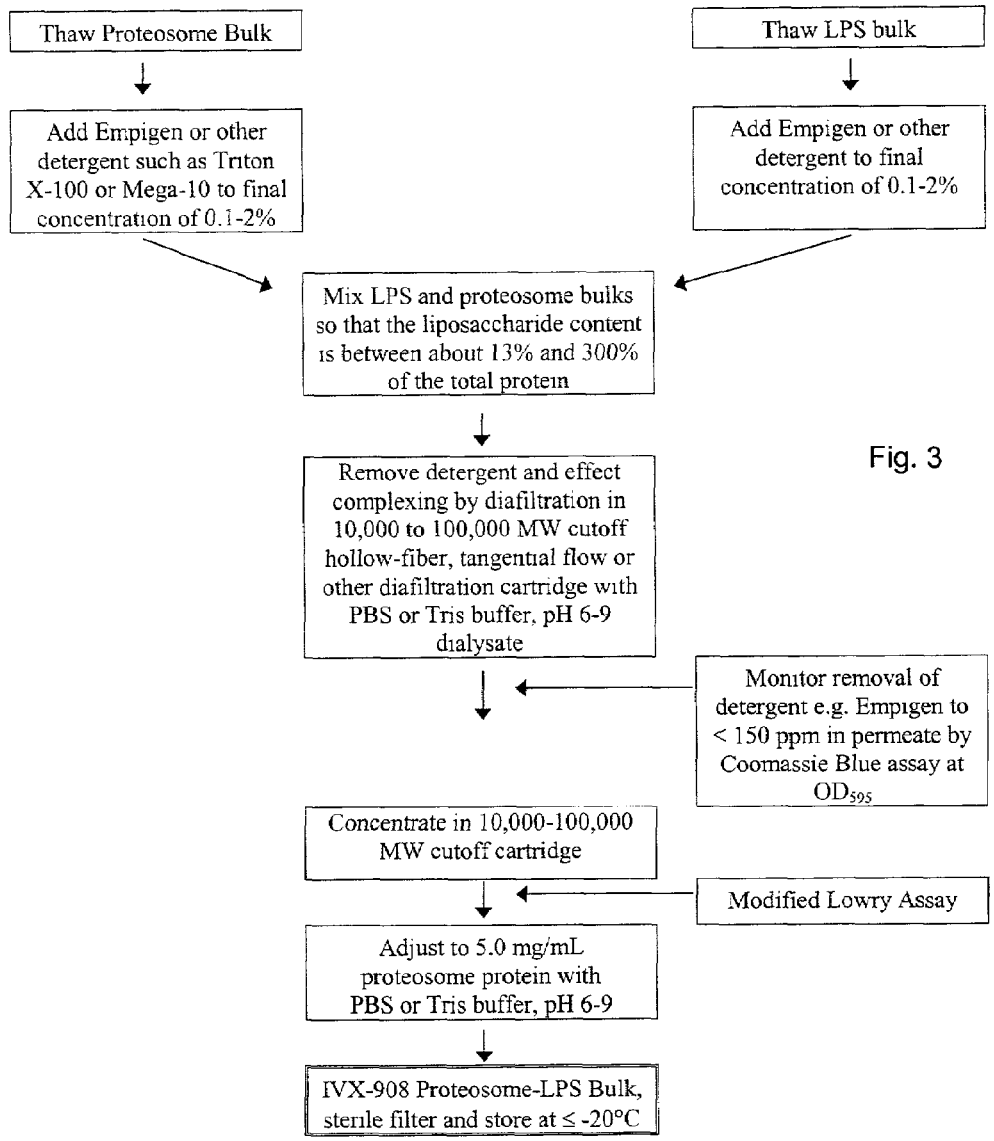
FIG. 3 shows a scheme for the manufacture of IVX-908 proteosome-LPS adjuvant (Flow Chart 3).

Two examples of outer membrane protein proteosome preparations are shown. These preparations were purified from type 2 Neisseria meningitidis by extraction of phenol-killed bacterial paste with a solution of 6% Empigen BB (EBB) (Albright and Wilson, Whithaven, UK) in 1 M calcium chloride followed by precipitation with ethanol, solubilization in 1% EBB-Tris/EDTA-saline and then precipitation with ammonium sulphate. The precipitates were re-solubilized in the 1% EBB buffer, diafiltered and stored in an EBB buffer at −70° C. A flow chart of this process, which resulted in proteosomes having a liposaccharide content of between 0.5% and 5%, is shown in Flowchart 1A (FIG. 1A) on the following pages. Proteosomes may also be prepared by omitting the ammonium sulphate precipitation step to shorten the process as desired with resultant proteosomes having a liposaccharide content of between 12% and 25%, and may, depending upon the materials, be between 15% and 20% as shown in Flowchart 1B (FIG. 1B).

Example 2

Production of Liposaccharides

The example in Flowchart 2 (FIG. 2) shows the process for the isolation and purification of LPS from *S. flexneri* or *P. shigelloides* bacteria. This process can similarly be used for preparing LPS from other gram-negative bacteria including, but not restricted to *Shigella*, *Plesiomonas*, *Escherichia* and *Salmonella* species. Following growth of the bacteria by fermentation, the cell paste was re-hydrated with 3 mL 0.9M NaCl, 0.005 M EDTA/g paste. Ten mg lysozyme/g paste was also added. Lysozyme digestion was allowed to proceed for 1 hour at room temperature. Fifty U/mL Benzonase (DNase) was then added with 0.025M $MgCl_2$. DNase digestion was allowed for 30 minutes to proceed at room temperature. The suspension was then cracked by passage through a microfluidizer at 14,000 to 19,000 psi. Fresh DNase (50 U/mL) was added and the suspension was digested for a further 30 min at room temperature. The digested cell suspension was heated to 68° C. in a water bath. An equal volume of 90% phenol (at the same temperature) was added and the mixture was incubated with shaking at 68° C. for 30 min. The mixture was centrifuged at 4° C. to separate the aqueous and organic phases. The aqueous phase was harvested and the organic phase was re-extracted with WFI (water for injection) at 68° C. for 30 min. The mixture was centrifuged at 4° C. to separate the aqueous and organic phases and the aqueous phases were combined. Twenty percent ethanol and 10 mM $CaCl_2$ were added to the combined aqueous phase to precipitate nucleic acids. The mixture was stirred at 4° C. overnight. Precipitated nucleic acids were then pelleted by centrifugation at 10,000 ×G for 30 minutes and the supernatant was collected.

The supernatant was concentrated and diafiltered using a 30,000 MW hollow fiber cartridge into 0.15M NaCl, 0.05M Tris, 0.01M EDTA and 0.1% Empigen BB, pH 8.0. Finally, the LPS was sterile-filtered using a 0.22 um Millipak 60 filter unit aliquoted into sterile storage containers and frozen at −80° C.

Example 3

Preparation and Characterisation of a Proteosome-Liposaccharide Adjuvant Complex The adjuvant is manufactured by non-covalently complexing Proteosomes to LPS. The LPS can be derived from any of a number of gram negative bacteria including, but not limited to *Shigella* or *Plesiomonas* or *Escherichia* or *Salmonella* species as described in Flowchart 3. Briefly, proteosomes and LPS were thawed overnight at 4° C. and adjusted to 1% Empigen BB in TEEN buffer. Proteosomes were thawed overnight and adjusted to 1% Empigen BB in TEEN buffer. The two components were mixed at quantities resulting in a final Proteosome:LPS wt/wt ratio of between 10:1 and 1:3 and stirred for 15 minutes at room temperature. The LPS-Proteosome mixture was diafiltered on an appropriately sized (e.g. Size 9) 10,000 MWCO hollow fiber cartridge into TNS buffer (0.05 M Tris, 150 mM NaCl pH 8.0). The diafiltration was stopped when Empigen content in the permeate was <50 ppm (by Empigen Turbidity Assay or by a Bradford Reagent Assay). The bulk adjuvant IVX-908 was concentrated and adjusted to 5 mg/mL protein (by Lowry assay). Finally, the adjuvant was sterile-filtered using a 0.22 um Millipak 20 filter unit. The bulk adjuvant was aliquoted into sterile storage containers and frozen.

The Proteosome-LPS complex was tested for Empigen (400 ppm) using reverse-phase HPLC; protein content by Lowry, LPS content by measurement of 2-keto-3-deoxyoctonate (KDO) assay. The said invention was further characterised for particle size distributions as determined by quantitative number weighted analysis using a particle sizer (Brookhaven Instruments model 90 plus or similar machine) (10-100 nm). However, the particle size for the complex will increase with a higher proteosome to LPS ratio. Stability of the complex formulations should be consistent with the previously demonstrated *S. flexneri* LPS vaccine. These data demonstrate complex stability at both refrigerated and accelerated temperature (25 and 37° C.).

Example 4

Preparation of IVX-908 Influenza Antigen or Birch Pollen Allergen or Ovalbumin Mixtures The current invention was prepared by mixing the IVX-908 Proteosome-LPS adjuvant (Example 3) with antigen in proportions that promote optimal formulations for stability and immunological outcomes.

Example 5

Mouse Immunization Protocols for Influenza Antigen Studies

BALB/c mice were immunized Intranasally or Intramuscularly on days 1 and 21 with antigens in volumes of 25 or 100□l respectively containing between 0.3 and 3ug influenza hemagglutinin (HA) as A/Beijing/262/95 or an A/Beijing/262/95 plus A/Sydney/5/97 bivalent detergent split antigen (GMP commercial licensed antigen) either alone or mixed with 0.3-3 ug IVX-908 adjuvant (containing LPS at various Proteosome:LPS wt/wt ratio). Control mice were given intranasal immunizations with phosphate buffered saline. Animals were bled on day 35 via the saphenous vein or by cardiac puncture. Nasal or lung lavage or vaginal washes were taken on day 35. The lungs of each mouse were surgically exposed and a canula inserted in the trachea. Using a syringe containing phosphate buffered saline supplemented with 0.1% bovine serum albumin and protease inhibitors (0.2 mM AEBSF, 1 □g/ml Aprotinin, 3.25 uM Bestatin and 10 uM Leupeptin), 1 nasal lavage sample (approximately 1 ml) and 2 lung lavage samples (2×1 ml) were collected. The lung lavage fluids from individual animals were combined, vortexed and centrifuged to remove cell debris, and supernatants stored at −70° C. until assayed by ELISA. Vaginal washes were performed by inserting a tampon wetted with 25 ul of supplemented phosphate buffered saline (as above), into the vagina of the mouse for 30 seconds. After removing the tampon, the procedure was repeated with the opposite end of the tampon. The tampon was stored frozen at −70° C. and reconstituted in ELISA blocking buffer (see Example 8) at time of assay.

Example 6

Serum Hemagglutination Inhibition Assay (HAI)

Prior to determination of HAI activity, mouse sera were heated at 56° C. to inactivate complement. Elimination of non-specific agglutination was achieved by treating mouse sera with receptor destroying enzyme (RDE). To 0.1 ml of serum was added 0.4 ml of RDE (100 units/ml) for 12 to 18 hr at 37° C. 0.3 ml of sodium citrate (2.5%) was added for 30 min at 56° C. to inactivate the RDE. The sample volume was made up to 1 ml with PBS (to give final sample dilution of 1:10). Two-fold serial dilutions of each sample were tested for their ability to inhibit the agglutination of 0.5% chick red blood cells by whole influenza virus in a standard HAI assay.

Example 7

Measurement of Specific Anti-flu Antibodies in Sera, in Lung, Nasal and Vaginal Fluids Sera were collected after each immunization; lung and nasal cavity lavage fluids and vaginal washes were collected after the last immunization. ELISA was performed using whole virus or detergent split antigen as the detecting antigen. Briefly, 96 well round bottom microtiter plates (e.g. Costar EIA/RIA 96 well Easywash Plates, Corning, N.Y.) were coated with antigen and incubated overnight. After aspiration of the antigen using a plate washer, plates were washed once with PBS containing 0.1% Tween (PBS-T) and incubated with blocking buffer containing PBS-T plus 2% powdered milk. After aspirating the blocking buffer and washing with PBS-T, samples of sera, lung or nasal cavity lavage fluids, or vaginal washes serially diluted 2-fold in blocking solution, were added and the plates were incubated for two hours at 37° C. After washing with PBS-T, affinity purified horseradish peroxidase (HRP)-labelled goat anti-mouse IgG or IgA was added and plates were incubated at 37° C. for 30 min. After aspirating and washing twice with PBS-T, developing solution was added and plates were incubated for 30 min at r.t. and stopped by addition of $H_2SO_4$ prior to determining the absorbance values using a microtiter ELISA plate reader (Molecular Devices, Menlo Park, Calif.). Antibody titers in the Tables are expressed as ng/ml of specific IgG or IgA determined from a standard curve produced using an ELISA capture assay using affinity purified mouse IgG and IgA standards (Sigma).

Example 8

Enhanced Immunogenicity and Immunity Elicited by IVX-908 Adjuvanted Influenza Vaccines This example shows the serum and mucosal antibody responses induced following nasal immunization with monovalent (A/Beijing/262/95) or nasal or intramuscular immunization with bivalent (A/Beijing/262/95 plus A/Sydney/5/97) antigens given with or without IVX-908 adjuvants. Mice received 2 doses of antigen containing 0.3 ug HA and IVX-908 (which IVX-908 consists of a 1:1 wt/wt proteosome to LPS ratio with 1.2 ug of proteosome protein for every 0.3 ug of HA) per strain of influenza antigen used. Anti-influenza IgG antibodies in sera were analysed by HAI; IgG in sera and IgA antibodies in lung and nasal cavity fluids were analysed by ELISA. Results are shown and summarised in Tables 1-3. Briefly:

IVX-908 Adjuvanted Influenza Vaccine given Nasally:

1. elicited between 50 to 250-fold higher serum IgG responses than the split Flu influenza antigen alone given nasally and up to 10-fold greater than the influenza vaccine given by injection (i.m.) (Tables 1-3), 2. elicited 16 to 100-fold higher serum HAI responses than split Flu alone given nasally and up to 8-fold higher than elicited by giving the split product influenza vaccine alone by injection (Tables 1-3),
3. elicited between 20 to 120-fold higher IgA responses in the nasal cavity than the split Flu influenza vaccine alone given nasally or by injection (i.m.) (Table 1),
4. elicited 50 to >600-fold higher specific IgA responses in the lung than split Flu influenza vaccine alone given nasally or by injection (i.m.) (Tables 1-3),
5. induced 30 to >160-fold increases in specific vaginal IgA compared with split Flu influenza vaccine alone given nasally or by injection (Table 2).

IVX-908 Adjuvanted Influenza Vaccine given Intramuscularly:
1. induces up to 5-fold increases in specific serum IgG and up to 8-fold increase in serum HAI compare to the split Flu influenza vaccine alone given by injection (table 3)

The data demonstrates that IVX-908 prepared with LPS from either *P. shigelloides* (Tables 1 and 3) or *S. flexneri* (Table 2) when mixed with influenza split antigens, enhances both the serum and mucosal antigen-specific immune responses. Furthermore, IVX-908 adjuvanted the HA-specific immune responses against each of the individual monovalent HA antigens when given as a multivalent preparation (Tables 2 and 3).

TABLE 1

Adjuvant effect of IVS-908 via the intranasal route with monovalent antigen. Murine serum HAI, IgG and mucosal IgA induced by split flu antigen (A/Beijing/262/95) mixed with IVX-908 adjuvant (3 ug HA per dose at 4:1 IVX-908:HA ratio) following nasal immunization.

|  | Split Flu + IVX-908 nasal | Split nasal | Split IM | PBS |
|---|---|---|---|---|
| Serum IgG (ng/mL)* | 3,205,360 | 24,774 | 290,844 | 250 |
| HAI (GMT)** | 640 | ≦10 | 160 | ≦10 |
| Lung IgA (ng/mL)* | 6,168 | 32 | 10 | 10 |
| Nasal IgA (ng/mL)* | 1,531 | 85 | 13 | 10 |

All samples taken 14 days post $2^{nd}$ immunization.
IVX-908 prepared with *P. shigelloides* LPS.
*are Geometric Means for 10 mice/group
**HAI for sera pooled from 10 mice/group

TABLE 2

Adjuvant effect via the nasal route with bivalent antigen. Murine anti-A/Beijing/262/95 (H1) serum HAI, IgG and mucosal IgA induced by bivalent split flu antigen (A/Beijing/262/95 H1 and A/Sydney/5/97 (H3) mixed with IVX-908 adjuvant (0.3 ug HA/strain per dose at 4:1 IVX-908:HA ratio) given nasally

|  | Split Flu + IVX-908 nasal | Split nasal | Split IM | PBS |
|---|---|---|---|---|
| A. Anti-A/Beijing/262/95 (H1) response | | | | |
| Serum IgG (ng/mL)* | 427,600 | 1,682 | 97,810 | 2000 |
| HAI (GMT)** | 160 | ≦10 | 20 | ≦10 |
| Lung IgA (ng/mL)* | 1,276 | 5 | 10 | 4 |
| Vaginal IgA (ng/mL)* | 833 | 8 | 5 | 4 |
| B. Anti-A/Sydney/5/97 (H3) response | | | | |
| Serum IgG (ng/mL)* | 32,835 | 643 | 84,712 | 2000 |
| HAI (GMT)** | 80 | ≦10 | 320 | ≦10 |
| Lung IgA (ng/mL)* | 358 | 4 | 4 | 4 |
| Vaginal IgA (ng/mL)* | 141 | 5 | 4 | 4 |

All samples taken 14 days post $2^{nd}$ immunization.
IVX-908 prepared with *S. Flexneri* LPS.
are Geometric Means for 10 mice/group
**HAI for sera pooled from 10 mice/group

TABLE 3

Adjuvant effect via the nasal or intramuscular route. Murine anti-A/Beijing/262/95 (H1) serum HAl, IgG and mucosal IgA induced by bivalent split flu antigen (A/Beijing/262/95 H1 and A/Sydney/5/97 (H3) mixed with IVX-908 adjuvant (0.3 ug HA/strain per dose at 4:1 IVX-908:HA ratio) given nasally or intramuscularly

|  | Nasal Immunization | | Muscular Immunization | | |
|---|---|---|---|---|---|
|  | Split Flu + IVX-908 | Split Flu | Split Flu + IVX-908 | Split Flu | PBS |
| A. Anti-A/Beijing/262/95 (H1) response | | | | | |
| Serum IgG (ng/mL)* | 313,369 | 1,682 | 488,665 | 97,810 | 2000 |
| HAI(GMT)** | 160 | ≦10 | 160 | 20 | ≦10 |
| Lung IgA (ng/mL)* | 1,006 | 5 | 16 | 10 | 4 |
| B. Anti-A/Sydney/5/97 (H3) response | | | | | |
| Serum IgG (ng/mL)* | 62,064 | 643 | 253,860 | 84,712 | 2,000 |
| HAI(GMT)** | 160 | ≦10 | 320 | 320 | 20 |
| Lung IgA (ng/mL)* | 200 | 4 | 10 | 4 | 4 |

All samples taken 14 days post $2^{nd}$ immunization.
Adjuvant prepared with *P. Shigelloides* LPS.
are Geometric Means for 10 mice/group
**HA1 for sera pooled from 10 mice/group

Example 9

The Shift of Immune Responses from Type 2 to Type 1 by Nasal Proteosome Influenza Vaccines Spleen cell cultures from mice immunized with Proteosome-LPS adjuvanted and non-adjuvanted influenza split antigens were analyzed for their production of T cell cytokines interferon gamma (IFN-γ) and IL-5 as an indicator of induction of Th1 or Th2 type immune responses, respectively. Briefly, Balb/c mice were immunized either intranasally or intramuscularly as described in Example 6 with a bivalent formulation containing 3 ug influenza HA from with A/Beijing/262/95 plus A/Sydney/5/97 with or without 24 ug IVX-908 Proteosome-LPS. Mice were euthanized 14 days after the second immunization and the spleens from 5 mice from each group were harvested and cells teased into a single cell suspension using a 100-μm nylon cell strainer (Becton Dickinson, N.J.). Spleen cells were cultured at $2.0\times10^6$ cells/ml (200 μl/well) in RPMI 1640 medium (Gibco BRL, Life technologies, Burlington, ON) containing 8% fetal bovine serum (heat-inactivated for 1 hr at 56° C.; Gibco BRL), 2 mM glutamine (Gibco BRL), 50 μM 2-mercaptoethanol (Sigma Chemical Co., St-Louis, Mo.) and 50 μg/ml gentamycin (Gibco BRL) with or without UV-inactivated, purified A/Beijing/265/95 (H1N1) and IVR-108 reassortant (H3N2) influenza viruses (NIBSC, Hertfordshire, UK) in 96-well cell culture cluster (Corning, N.Y.). Cells were incubated for 72 hrs at 37° C. and supernatants harvested and frozen at −80° C. Murine cytokines levels were measured using sandwich ELISA kits (OptEIA set, purchased from pharmingen, San Diego, Calif.) according to manufacturer's instructions. Recombinant cytokines were used as standards.

Briefly, results in Table 4 demonstrate that IVX-908 given together with a multivalent bivalent split flu antigen to form an adjuvanted influenza vaccine given either nasally or intramuscularly induces uniquely the type 1 cytokine, INF □, without detectable IL-5, a type 2 cytokine. Conversely, bivalent influenza antigen alone given nasally or intramuscularly induces a mixed type 1 and type 2 immune response as evidenced by the production of both INF-γ and IL-5. These results indicate that IVX-908 induces enhanced antigen-specific serological responses and biases T cell responses against antigens towards the type 1 of immunity. Type 1 immune responses are important for the clearance of intracellular pathogens, for the development of anti-tumor responses and in the control of allergic responses.

TABLE 4

Murine cytokine induction from spleen cells. Mice were immunized with bivalent split flu antigen (A/Beijing/262/95 H1 and A/Sydney/5/97 H3) and IVX-908 adjuvant (3 ug HA/strain per dose at 4:1 IVX-908:HA ratio) given nasally or intramuscularly. IVX-908 adjuvant was prepared with *P. shigelloides* LPS. Spleen cells were re-stimulated with whole inactivated A/Beijing/262/95 (H1) or a Sydney (H3) reassortant.

|  | Nasal Immunization | | Muscular Immunization | |
| --- | --- | --- | --- | --- |
| Cytokine (pg/mL) | Split Flu + IVX-908 | Split Flu | Split Flu + IVX-908 | Split Flu |
| A. A/Beijing/262/95 (H1) immunization and re-stimulation | | | | |
| INF-γ | 6934 | 272 | 171 | 834 |
| IL-5 | 0 | 173 | 0 | 277 |
| B. A/Sydney/5/97(H3) immunization and re-stimulation | | | | |
| INF-γ | 9,690 | 0 | 2,657 | 4111 |
| IL-5 | 0 | 635 | 0 | 820 |

INF-γ and IL-5 were determined in supernatants of mouse spleen cells re-stimulated as described in Example 10 with whole inactivated virus (1.25 ug/mL) and are expressed in pg/mL of culture supernatant. Results are the means of triplicate cultures, and have had the values obtained for IFN-γ and IL-5 (pg/mL) from spleen cells of PBS immunized mice already subtracted.

Example 10

Defining Optimal Amounts and Ratios of IVX-908 and Hemagglutinin Antigen to Maximise Adjuvantation Mice were immunized i.n. on days 0 and 14 with 1ug of HA (H3N2 strain, A/Sydney/5/97) mixed with IVX-908 (proteosome protein: S. flex LPS, 1:1) in decreasing amounts from 10 ug to 0.03 ug. A subsequent study varied the amount of HA from 3 to 0.3 ug while keeping the amount of IVX-908 constant at 1 or 0.3 ug. In both studies, blood, lung lavage, nasal wash fluid and spleens were collected at euthanasia on day 21 and analyzed for IgG or IgA content, or used to prepare splenocytes for in vitro stimulation as appropriate (as described in Example 9 above). Significance of the data was assessed by ANOVA analysis using Tukey-Kramer pair-wise comparisons.

Figure 4A:
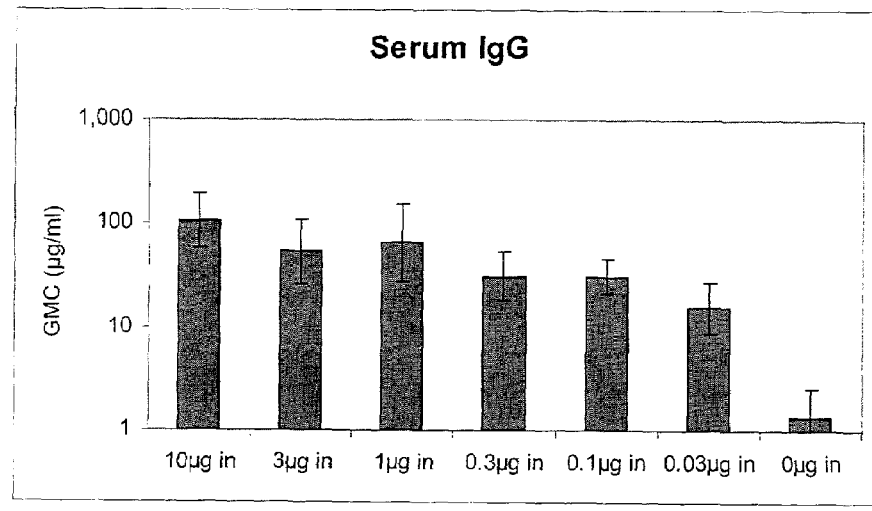
FIGS. 4*a*) and *b*) show the levels of specific serum IgG (a) and lung lavage IgA (b) elicited when a constant amount of HA was mixed with different amounts of IVX-908 and used to immunize mice intranasally.
Figure 4B:
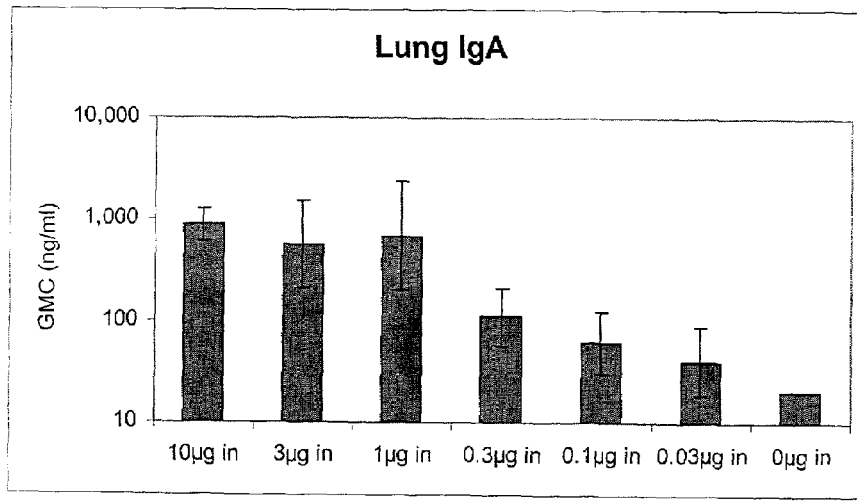
FIGS. 4*c*) and *d*) show the levels of specific serum IgG (c) and lung lavage IgA (d) elicited when a constant amount of IVX-908 (either 1 or 0.3 ug) was mixed with different amounts of HA and used to immunize mice intranasally.
Figure 4C:
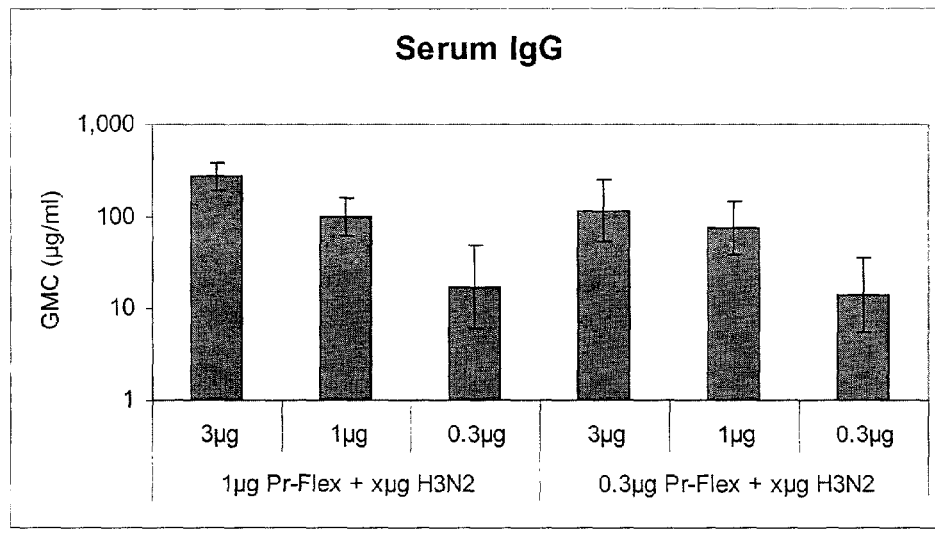
Figure 4D:
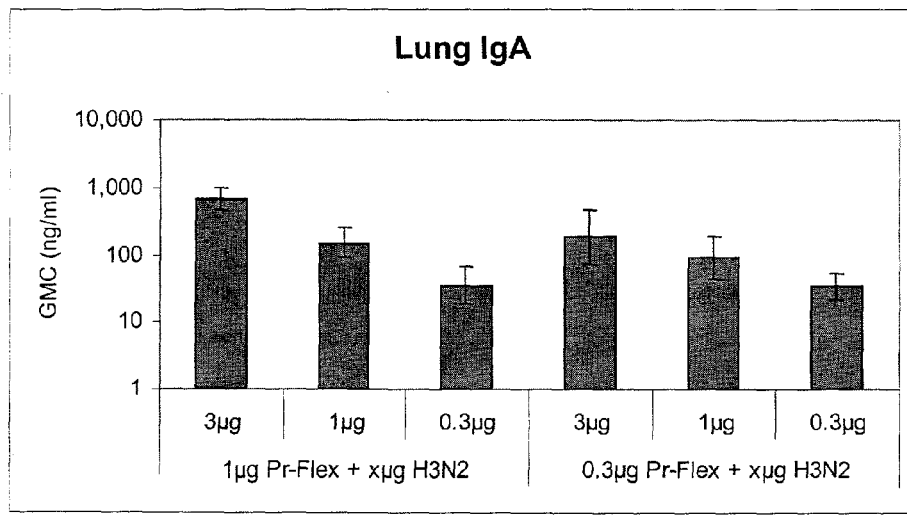

FIGS. 4a) and b) show that above a threshold at 0.3-1 ug of IVX-908, the elicited immune responses leveled-off, and below this threshold, the elicited responses diminished significantly. Keeping the amount of IVX-908 constant at this threshold, a second study was performed varying the amount of HA between 3 ug and 0.3 ug. The results in FIGS. 4c) and d) show that maximal systemic and mucosal immune responses were obtained when HA was mixed with IVX-908 above a threshold of 1-3□g of HA (administered i.n. with either 0.3 ug or 1 ug of IVX-908). The results indicate that in order to elicit optimal immune responses in mice, 1-3 ug of HA should be mixed with 0.3-1 ug of IVX-908.

As in other studies, analysis of the cytokines released from in vitro stimulated splenocytes showed that i.n. administration of HA with IVX-908 elicited responses primarily of type 1 phenotype.

Example 11

Enhancement of Systemic and Mucosal Immune Responses, and Protection Against Live Virus Challenge, Elicited by Intranasal Administration of Recombinant Hemagglutinin Mixed with IVX-908

Baculovirus-derived recombinant influenza hemagglutinin (rHA; H1N1 strain A/Texas/36/91), supplied as a full-length uncleaved protein (HA0), was purchased from a commercial source. The immunogenicity of the rHA was assessed by immunization of groups of 15, 6-8 week old female BALB/c mice. For intranasal (i.n.) immunizations, mice were lightly anesthetized, 25 ul of vaccine containing 2□ g of rHA with or without IVX-908 (8 ug proteosome protein and 8 ug S. flex LPS), or PBS was applied to the nares (12.5□l per nostril) and the mice allowed to inhale the droplets. Intramuscular (i.m.) immunization was achieved by injection of 25 ul (2 ug rHA) into the hind limbs. All mice were immunized on days 0 and 21. Ten animals from each group were challenged on day 48 by i.n. instillation of 8 $LD_{50}$ of mouse-adapted homotypic variant influenza virus (A/Taiwan/1/86) to assess protection. Any deaths were recorded, and weight loss was used as a surrogate for morbidity; mice were weighed immediately before and every 2 days after challenge. Mice losing ≧30% of their pre-challenge body weight or showing a lesser weight loss (≧20%) in conjunction with other clinical signs of distress and/or morbidity (e.g. pilo-erection, hunched posture, reduced mobility) were deemed to have met the experimental endpoint criteria and were euthanized. The 5 non-challenged mice from each group were euthanized on day 51 and exsanguinated by cardiac puncture. Serum was separated from clotted blood and stored at −70° C. until assay. Spleens were removed aseptically and processed for in vitro re-stimulation (as described in Example 9 above). Nasal washes and lung lavage were performed as previously described.

Figure 5A:
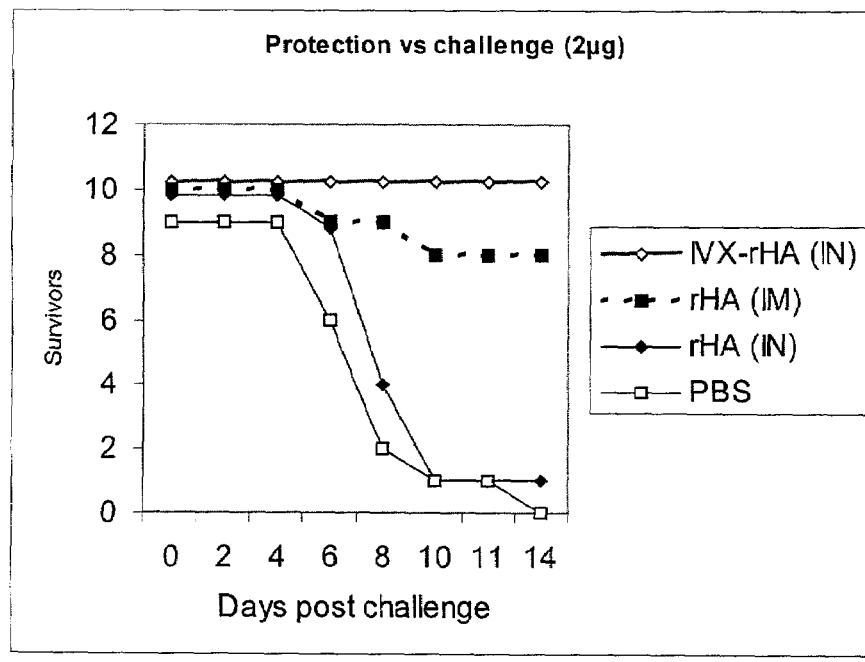
FIG. 5*a*) shows the numbers of immunized (n=10) or control (n=9) mice surviving challenge with a live, mouse-adapted, homotypic variant influenza virus.

Table 5a shows the systemic and mucosal responses in samples collected on day 51, and Table 5b shows the amounts of IFN-γ and IL-5 released from splenocytes following specific in vitro stimulation. FIG. 5a) shows the protection against mortality, and b) protection against morbidity, in immunized or control mice following challenge with live, homotypic variant, mouse-adapted virus.

The Results Demonstrate that:
1. Serum responses elicited by IVX-908+rHA were 4× and 100× higher respectively than the responses induced by rHA alone given i.m. or i.n.
2. Only i.n. rHA administered with IVX-908 elicited detectable mucosal IgA responses.
3. I.n. immunization with IVX-908+rHA induced responses of type 1 phenotype in contrast to i.m. rHA alone which induced responses of type 2 phenotype.
4. In contrast to rHA immunized or control mice, all mice (10/10) immunized i.n. with IVX-908+rHA survived live virus challenge. 8/10 and 1/10 mice immunized i.m. or i.n. with rHA alone survived whilst no control mice survived.
5. Mice immunized i.n. with IVX-908+rHA suffered no weight loss following challenge. The surviving mice immunized with rHA alone by either i.n. or i.m. routes, all lost significant amounts of weight, indicating morbidity as a result of infection following challenge. Thus i.n. IVX-908+rHA protected mice against morbidity as well as mortality following challenge.

Example 12

Induction of Serum and Mucosal Antibodies and Shift of Immune Responses from Type 2 towards Type 1 by Nasal IVX-908/Bet v 1a Allergen Formulation Recombinant Bet v 1a protein was expressed in *E. Coli* with a His-Tag (His) added at the amino terminus and purified by affinity chromatography on nickel columns. BALB/c mice were immunized intranasally (in volumes of 28 μl (Table 6) or 36 μl (Table 7) three times at two (Table 7) or three (Table 6) weeks apart with either 10 μg Bet v 1a as purified recombinant protein (rBet v 1a) or birch pollen extract (BPEx) (Greer Labs. Inc.) alone or as a mixture of 10 μg rBet v 1a or BPEx plus 10 μg of IVX-908 (Tables 6 and 7). Control mice were given intranasal immunizations with phosphate buffered saline (PBS). Other mice were given 10 μg Bet v 1a in 2 mg aluminum phosphate intraperitoneally in a volume of 150 μl on days 0 and 21 (Table 6), or 3 μg birch pollen extract (BPEx) (Greer Labs. Inc.) in 1 mg aluminum phosphate on day 0 (Table 7). One (Table 6) or three (Table 7) weeks after the final immunization, animals were bled by cardiac puncture subsequent to obtaining lung lavage fluids. Bet v 1a-specific IgE (OptEIA Mouse IgE Set; BD Pharmingen, Mississauga, Ontario), IgG, IgG1 and IgG2a in serum, and IgA and total IgA in broncho-alveolar lavages were measured by ELISA. The levels of secreted IFN-γ and IL-5 were determined in the supernatants from spleen cell cultures (10×10$^6$ splenocytes/mL) after two and three days respectively following re-stimulation in vitro with 10 μg/ml Bet v 1a. Cytokines were detected by ELISA (BD Pharmingen; Mississauga, Ontario). In table 8, an example is shown for cytokine induction in mice injected intraperitoneally on day 71 with a single dose of 10 μg rBet v 1a in 2 μg aluminum phosphate following 3 nasal immunizations on days 0, 17 and 29 with 10 μg birch pollen extract (BPEx) (Greer Labs. Inc.) alone or as a mixture with 10 μg of IVX-908 In Table 9, an example is shown for cytokine induction following 3 immunizations of rBet v 1a or BPEx with or without IVX-908 in mice previously sensitized intraperitoneally with a single dose of 10 μg Bet v 1a in 2 mg aluminum phosphate.

Results for T cell cytokine and serum and mucosal immunoglobulin responses following intranasal immunization with an IVX-908/rBet v 1a or an IVX-908/BPEx mixture are shown in Tables 6, 7, 8 and 9.

IVX-908 Adjuvanted rBet v 1a or BPEx given Nasally to Naïve Mice (Tables 6 and 7):
1. directed the T cell response induced by Bet v1a allergen from a type-2 biased to a higher or predominantly type-1 phenotype. This was due to the enhanced production of Table 5a shows the systemic and mucosal responses elicited by immunization of mice with 2 ug of rHA, with or without IVX-908, as described in example 11. HI titer is the reciprocal of the maximum dilution of serum which will inhibit hemagglutination, and immunoglobulin levels (IgG or IgA) are expressed as Geometric Mean Concentrations with 95% confidence limits in parentheses. ND = not detected.

|  | IVX-908 + rHA (IN) | rHA (IM) | rHA (IN) | PBS |
|---|---|---|---|---|
| HI titer | 1280 | 320 | 10 | 10 |
| Serum IgG (ug/ml) | 109.3 (51.5-232.3) | 25.0 (12.1-51.4) | 1.1 (0.9-1.4) | 1.0 |
| Nasal IgA (ng/ml) | 77 (30-196) | ND | ND | ND |
| Lung IgA (ng/ml) | 265 (112-629) | ND | ND | ND |

Table 5b shows the amounts (pg/ml; determinations performed in triplicate) of IFN-γ and IL-5 released into culture supernatants following in vitro stimulation of splenic T cells from mice immunized with 2 ug of vaccine or control material. Splenocytes were restimulated with inactivated mouse-adapted A/Taiwan influenza virus.

|  | IVX-908 + rHA | rHA (IM) | rHA (IN) | PBS |
|---|---|---|---|---|
| IFN-γ (pg/ml) | 12960 | 2918 | 3081 | 3266 |
| IL-5 (pg/ml) | 3 | 34 | 3 | 3 |

IFN-γ by spleen cells from mice given IVX-908 formulated allergen compared to rBet v 1a or BPEx alone or with aluminum phosphate with a lowering (for IVX-908/BPEx) or maintenance (for IVX-908/rBet v 1a) of the production of IL-5,
2. enhanced production of Bet v 1a-specific serum IgG compared with rBet v 1a or BPEx given alone, and,
3. produced a 37-43 fold reduction in levels of serum IgE levels compared with that induced by rBet v 1a in aluminium phosphate, an immunizing regime known to sensitize animals for allergic responses on subsequent challenge with antigen.

TABLE 6

Induction of murine cytokines and serum and mucosal antibodies by 10 ug rBet v 1a alone or formulated with IVX-908 (10 ug 1:1 protein:LPS) via the nasal route, or with 2 mg aluminium phosphate by the intraperitoneal route as described in Example 10.

|  | rBet v 1a | rBet v 1a + IVX-908 | rBet v 1a + Alum | PBS |
|---|---|---|---|---|
| IFN-γ (pg/mL) | 53 | 2,598 | 35 | 0 |
| IL-5 (pg/mL) | 965 | 905 | 1,746 | 0 |
| IL-5/IFN-γ ratio | 18 | 0.4 | 50 | 0 |
| Serum IgE (ng/mL) | 8 | 77 | 2,832 | 8 |
| Serum IgG (ng/mL) | 27 | 11,111 | 901,497 | 3.8 |
| Lung IgA/total IgA (%) | 1.3 | 0.4 | 1.7 | 0.4 |

Results for IFN-γ and IL-5 are expressed as the mean pg/mL for triplicate cultures from spleens pooled from 5 mice/group. Serum IgG is expressed as the sum of IgG1 and IgG2a titers. Lung IgA is shown as specific IgA expressed as % total IgA. All immunoglobulin titers were calculated using geometric mean titers for samples from 7 to 10 (IgG and IgE) or 5 (IgA) mice/group. IVX-908 was prepared with *S. flexneri* LPS.

TABLE 7

Induction of murine cytokines and serum IgG by 10 ug birch pollen extract (BPEx) alone or formulated with 10 ug IVX-908 via the nasal route as described in Example 12. For BPEx + alum, mice were given a single i.p. immunization of 3 ug birch pollen extract together with 1 mg aluminum phosphate.

|  | BPEx | BPEx + IVX-908 | BPEx + Alum | PBS |
|---|---|---|---|---|
| IFN-γ (pg/mL) | <10 | 435 | 142 | 0 |
| IL-5 (pg/mL) | 431 | 143 | 290 | 0 |
| IL-5/IFN-γ ratio | >43.1 | 0.33 | 2 | 0 |
| Serum IgE (ng/mL) | 16 | 19 | 829 | 16 |
| Serum IgG (ng/mL) | 105 | 2,300 | nd | 7.5 |

Results for IFN-γ and IL-5 are expressed as the mean pg/mL for triplicate cultures from spleens pooled from 4-5 mice/group. Serum IgG is for sera pooled from 15 mice except for the BPEx+IVX-908 group where the geometric mean of results from 15 individual mice were calculated. Serum IgE for the BPEx+IVX-908 group represents the geometric means from sera from 15 individual mice while BPEx+Alum results are geometric means for 86 individual mice. Serum IgE levels for BPEx and PBS were measured in sera pooled from 15 animals. IVX-908 was prepared with *S. flexneri* LPS.

IVX-908 Adjuvanted BPEx given Nasally to Mice and Subsequently Injected with rBet v 1a plus Alum (Table 8):
1. increased the production of the type 1 cytokine, IFN-γ by 10-fold compared with BPEx given alone
2. and slightly lowered the levels of the type 2 cytokine, IL-5.

TABLE 8

Induction of cytokines in mice injected intraperitoneally with rBet v1a plus alum following 3 nasal immunizations with 10 ug birch pollen extract alone or formulated 1:1 with IVX-908 (10 ug protein:LPS) as described in Example 12.

|  | BPEx | BPEx + IVX-908 |
|---|---|---|
| IFN-γ (pg/mL) | 31 | 330 |
| IL-5 (pg/mL) | 384 | 276 |
| IL-5/IFN-γ ratio | 13 | 0.8 |

Results for IFN-γ and IL-5 are expressed as the geometric means (pg/mL) from spleen cultures from 8-10 individual mice/group. IVX-908 was prepared with *S. flexneri* LPS.

IVX-908 Adjuvanted rBet v 1a or BPEx given Nasally to rBet v 1a Sensitized Mice (Table 9):
1. increased the production of the type 1 cytokine, IFN-γ by 4.7- and 33-fold for IVX-908/rBet v 1a and IVX-908/BPEx respectively compared with the corresponding allergens alone and
2. lowered the levels of the type 2 cytokine, IL-5

TABLE 9

Induction of murine cytokines by 10 ug rBet v 1a or birch pollen extract given nasally alone or with 10 ug IVX-908 in rBet v 1a-sensitized mice as described in Example 12.

|  | rBet v 1a | rBet v 1a + IVX-908 | BPEx | BPEx + IVX-908 | PBS |
|---|---|---|---|---|---|
| IFN-γ (pg/mL) | 126 | 593 | 295 | 9790 | 55 |
| IL-5 (pg/mL) | 2353 | 1747 | 8160 | 6270 | 460 |
| IL-5/IFN-γ ratio | 19 | 3 | 28 | 0.6 | 8 |

Results for IFN-γ and IL-5 are expressed as the geometric means (pg/mL) from spleen cultures from 4-5 mice/group. IVX-908 was prepared with *S. flexneri* LPS.

The data in Tables 6, 7, 8 and 9 demonstrate that allergens (purified recombinant proteins or extracts) formulated with IVX-908 induce type 1 immune responses in mice. These formulations maintained the production of type 1 cytokines in mice subsequently injected intraperitoneally with a sensitizing injection of rBet v 1a plus alum. Importantly, these formulations also enhanced the production of type 1 cytokines in mice that had previously been sensitized or made allergic to the allergen. These results suggest the potential utility of IVX-908/allergen formulations as therapeutic vaccines for allergic diseases.

Example 13

Enhancement of Immune Responses Against a Poor Immunogen

Figure 6:
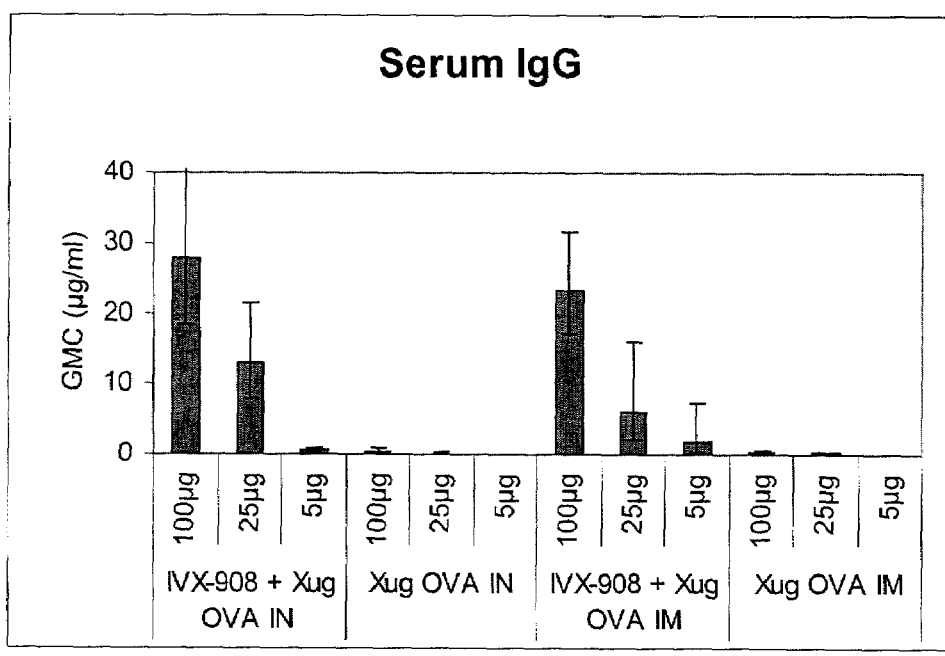
FIG. 6 shows specific antibody responses in serum of mice immunized i.n. or i.m. with Ovalbumin with or without IVX-908. Titers are expressed as geometric mean concentrations of specific IgG (ug/ml) with 95% confidence limits indicated by error bars.

Mice were immunized as above by either the i.n. or i.m. routes, with Ovalbumin (OVA—a poorly immunogenic, soluble protein) in decreasing amounts from 100 ug to 5 ug, with or without 1 ug of IVX-908 ( proteosome protein:LPS 1:1, using P. shig LPS). Following immunization on days 0 and 14, mice were euthanized on day 21 and serum, lung lavage fluids and spleens collected for analysis. Serum GMCs are shown in FIG. 6.

The data confirms that unadjuvanted OVA is poorly immunogenic and elicited barely detectable serum IgG titers even when mice were immunized with 100 ug of OVA by either i.n. or i.m. routes. However when mixed with IVX-908, over 60-fold rises in titers were observed by both routes of immunization, albeit at higher concentrations (≧25 ug) of OVA. No mucosal responses were detected in any of the immunized mice. Analysis of the cytokine profiles elicited by OVA or OVA+IVX-908 showed that when immunized i.n., co-administration of IVX-908 induced the secretion of elevated levels of IFN-γ, IL-2, IL-4 and IL-5 from splenocytes. Thus unlike HA which induced release of cytokines indicative of a type 2 phenotype response which switched to a type 1 phenotype when HA was administered with IVX-908, adjuvanting of the poorly immunogenic, soluble OVA appeared to be associated with induction of a balanced type 1/type 2 phenotype response.

Example 14

Effect of Varying the Amount of LPS in IVX-908 on Elicited Immunity

To determine the effects of varying the ratio of proteosome to LPS in IVX-908 on elicited immunity, a study was performed in which mice were immunized i.n. as above with 3 ug of HA (H3N2 strain A/Sydney) mixed with 1 ug (as LPS) of IVX-908 (1:1 or 1:2 complex of proteosomes and *P. shigelloids* LPS). At euthanasia, blood and lung washes were collected and analyzed by ELISA for specific IgG or IgA respectively. The results are shown in table 9, and indicate that although both IVX-908s elicit virtually identical levels of specific serum IgG, there is a highly significant difference (P≦0.001) between the mucosal IgAs elicited by the different IVX-908s. Clearly the IVX-908 comprising proteosomes complexed 1:1 with *P.shigelloids* LPS elicited higher titers of specific mucosal IgA in lung lavage fluids and therefore possesses more mucosal adjuvant activity than the 1:2 proteosome protein:LPS complex.

Table 9 shows immunoglobulin levels (IgG or IgA) expressed as geometric mean concentrations with 95% confidence limits in parentheses, in serum and lung washes from mice immunized i.n. with HA + IVX-908 (Pr:LPS 1:1 or 1:2).

|  | IVX908 (Proteosome protein:LPS, 1:2) | IVX908 (Proteosome protein:LPS, 1:1) |
|---|---|---|
| Serum IgG (ug/ml) | 158.8 (105.4-239.2) | 166.8 (108.5-256.3) |
| Lung IgA (ng/ml) | 393 (157-981) | 2026 (1230-3335) |

Example 15

Adjuvant Effects of IVX-908 Prepared with LPS from Different Organisms.

To determine the adjuvanticity of IVX-908 made by complexing proteosomes to LPS from novel organisms, IVX-908 preparations were made using LPS from a non-pathogenic *E. coli* (O17) and from *Salmonella* essen. IVX-908 preparations were made by mixing proteosomes and the LPS in 3:1, 1:1 and 1:3 (w/w) ratios in the presence of Empigen, and removal of detergent by dialysis in dialyzing cassettes. Mice were immunized i.n. on day 0 and 14 with 3 ug of HA (B/Guangdong) mixed with 3 ug or 0.3 ug (as LPS) of IVX-908. Control mice received 3 ug HA i.n. At euthanasia on day 21, blood was collected and analyzed by ELISA for specific IgG. The results are shown in Table 10, and indicate that IVX-908 preparations made with LPS from pathogens other than *Shigella* species are capable of enhancing immune responses to a vaccine antigen. For IVX-908 prepared with *E. coli* LPS, the 1:1 and 1:3 ratios of proteosomes to LPS at a dose of 0.3 ug LPS gave significant (P≦0.001) enhancement of the anti-HA serum IgG response compared with HA alone given i.n. All ratios of Pr:LPS (S. essen) at both doses tested elicited significant (P≦0.001) enhancement of serum anti-HA responses over HA alone given i.n. The results for IVX-908 made with *S. essen* were comparable to those obtained for IVX-908 made with LPS from *Shigella* species.

Table 10 shows serum anti-HA IgG titers expressed as geometric mean concentrations (ug/ml) with 95% confidence limits in parentheses for 8 mice per group immunized i.n. with HA + IVX-908 preparations containing LPS from different gram negative bacteria and at different Pr:LPS ratios

| Immunogen | Serum IgG (ug/ml) Pr:LPS ratio | | |
|---|---|---|---|
|  | 3:1 | 1:1 | 1:3 |
| HA + Pr:*E. coli* LPS (0.3 ug LPS) | 0.83 (0.79-0.87) | 4.75 (2.53-8.91) | 38.93 (28.19-53.75) |
| HA + Pr:*S. essen* LPS (0.3 ug LPS) | 19.89 (12.12-32.63) | 28.24 (18.14-43.98) | 22.91 (13.43-39.09) |
| HA + Pr:*S. essen* LPS (3 ug LPS) | 76.41 (43.62-133.86) | 38.52 (20.64-71.9) | 69.05 (31.15-153.04) |
| HA + Pr:*P. shig* LPS (3 ug LPS) |  | 38.97 (16.53-91388) |  |
| HA + Pr:*S. flex* LPS (3 ug LPS) |  | 19.19 (7.39-49.8) |  |
| HA | 0.83 (0.77-0.89) |  |  |

To the extent necessary to understand or complete the disclosure of the present invention, all publications, patents, and patent applications mentioned herein are expressly incorporated by reference therein to the same extent as though each were individually so incorporated.

The invention claimed is:

1. An immunogenic composition for inducing an immunological response to an antigen, said composition comprising the antigen and an effective amount of proteosome-lipopolysaccharide adjuvant, wherein the proteosome-lipopolysaccharide adjuvant enhances the immunological response to the antigen, wherein the antigen and the proteosome-lipopolysaccharide adjuvant are separate chemical entities, and wherein the proteosome-lipopolysaccharide adjuvant is formed from an outer membrane proteosome complexed with a lipopolysaccharide preparation, wherein both the proteosome and the lipopolysaccharide preparation are from gram-negative bacteria, which proteosome-lipopolysaccharide adjuvant has a final lipopolysaccharide content by weight as a percentage of the total proteosome protein of at least 13%.

2. The immunogenic composition of claim 1 wherein the antigen is selected from a peptide, a protein, a toxoid, a glycoprotein, a glycolipid, a lipid, a carbohydrate, and a polysaccharide.

3. The immunogenic composition of claim 1 wherein the antigen is derived from a biologic or infectious organism of the animal or plant kingdom, is an allergen or a chemically or biologically modified allergen, or is a chemical material.

4. The immunogenic composition of claim 1 wherein the antigen is whole or disrupted microorganisms selected from viruses, bacteria and parasites, wherein the whole or disrupted microorganism are attenuated and/or inactivated.

5. The immunogenic composition of claim 1 wherein the antigen is produced by a synthetic procedure or a recombinant molecular procedure.

6. The immunogenic composition of claim 1 wherein the antigen is Bet v 1a.

7. The immunogenic composition of claim 1 wherein the antigen is rBet v 1a.

8. The immunogenic composition of claim 1 wherein the antigen is recombinant influenza antigen.

9. The immunogenic composition of claim 1 wherein the antigen is influenza split antigen.

10. The immunogenic composition of claim 1 wherein the antigen is birch pollen extract.

11. The immunogenic composition of claim 1 wherein the antigen is an immunogen extract.

12. The immunogenic composition of claim 1 wherein the immunogenic composition is a specific immunotherapeutic, adjuvanted prophylactic vaccine or therapeutic vaccine.

13. A process for inducing an immune response comprising administering the immunogenic composition of any one of claims 1-12 to a subject.

14. The process of claim 13 wherein the composition is administered by a route selected from the group consisting of mucosal, enteral, parental, transdermal/transmucosal, and inhalation.

15. The process of claim 14 wherein the mucosal route is via the nasal, oropharyngeal, ocular, or genitourinary mucosa.

16. The process of claim 14 wherein the enteral route is oral, rectal or sublingual.

17. The process of claim 14 wherein the parenteral route is any one of intraarterial, intradermal, intramuscular, intraperitoneal, intravenous, subcutaneous, and submucosal injection or infusion.

18. The process of claim 14 wherein the transdermal/transmucosal route is topical.

19. The process of claim 14 wherein the inhalation route is intranasal, oropharyngeal, intratracheal, intrapulmonary or transpulmonary.

20. The process of claim 13 wherein the enhanced immune response includes one or more of the following: a) serum IgG antibodies or serum antibodies measured in functional assays; b) mucosal antibodies including IgA in mucosal secretions collected from respiratory, gastrointestinal or genitourinary tracts and c) correlates of cell-mediated immunity (CMI) including a shift from higher or predominant Type 2 responses to mixed, balanced, increased or predominant Type 1 responses as measured by cellular or antibody assays or Type 1 cytokine assays such as IFN-γ with maintained, decreased or absent Type 2 cytokines such as IL-5.

* * * * *

UNITED STATES PATENT AND TRADEMARK OFFICE
CERTIFICATE OF CORRECTION

| | | |
|---|---|---|
| PATENT NO. | : 7,524,509 B2 | Page 1 of 2 |
| APPLICATION NO. | : 10/094424 | |
| DATED | : April 28, 2009 | |
| INVENTOR(S) | : David S. Burt et al. | |

It is certified that error appears in the above-identified patent and that said Letters Patent is hereby corrected as shown below:

Title Page; Item 60 Related U.S. Application Data:
Insert --Provisional application No. 60/274,232, filed Mar. 9, 2001, provisional application No. 60/327,297, filed Oct. 9, 2001-- has been omitted from the face of the patent.

Title Page; Item 56 References Cited, Other Publications:
"Mallett et al. (Infection and Immunity, Jun. 1995, p.2382-2386)." should read, --Mallett et al. (Infection and Immunity, 63(6), Jun. 1995, p.2382-2386).--.

Title Page; Item 56 References Cited have been Omitted from the face of the patent:
--Qureshi et al., "Purification and Structural Determination of Nontoxic Lipid A Obtained from the Lipopolysaccharide of *Salmonella Typhimurium*," *The Journal of Biological Chemistry* 257(19):11808-11815, 1982.
Levenson et al., "Protection against Local *Shigella sonnei* Infection in Mice by Parenteral Immunization with a Nucleoprotein Subcellular Vaccine," *Infection and Immunity 63*(7):2762-2765, 1995.
Fries et al., "Safety and Immunogenicity of a Proteosome-*Shigella flexneri* 2a Lipopolysaccharide Vaccine Administered Intranasally to Healthy Adults," *Infection and Immunity 69*(7):4545-4553, 2001.
Jeannin et al., "OmpA targets dendritic cells, induces their maturation and delivers antigen into the MHC class I presentation pathway," *Nature Immunology 1*(6):502-509, 2000.
Pridmore et al., "A Lipopolysaccharide-Deficient Mutant of *Neisseria meningitidis* Elicits Attenuated Cytokine Release by Human Macrophages and Signals via Toll-like Receptor (TLR) 2 but Not via TLR4/MD2," *The Journal of Infectious Diseases 183*:89-96, 2001.
Massari et al., "Cutting Edge: Immune Stimulation by Neisserial Porins Is Toll-Like Receptor 2 and MyD88 Dependent," *The Journal of Immunology 168*:1533-1537, 2002.
Dalseg et al., "Outer Membrane Vesicles from Group-B Meningococci Can Act as Mucosal Adjuvant for Influenza Antigens," in Fred Brown (ed.), *Vaccines 96: Molecular Approaches to the Control of Infectious Diseases*, Cold Spring Harbor Laboratory Press, 1996, pp. 177-182.--.

Signed and Sealed this
Eleventh Day of October, 2011

David J. Kappos
*Director of the United States Patent and Trademark Office*

Title Page; Item 56 References Cited have been Omitted from the face of the patent:
--5,985,284 A 11/16/1999 Lowell 424/234.1
WO 97/10844 A1 03/27/1997
Mallett et al., "Intranasal or Intragastric Immunization with Proteosome-*Shigella* Lipopolysaccharide Vaccines Protects against Lethal Pneumonia in a Murine Model of *Shigella* Infection," *Infection and Immunity 63*(6):2382-2386, 1995.
Orr et al., "Immunogenicity and Efficacy of Oral or Intranasal *Shigella flexneri* 2a and *Shigella sonnei* Proteosome-Lipopolysaccharide Vaccines in Animal Models," *Infection and Immunity 61*(6):2390-2395, 1993.
Bhattacharjee et al., "A Noncovalent Complex Vaccine Prepared with Detoxified *Escherichia coli* J5 (Rc Chemotype) Lipopolysaccharide and *Neisseria meningitidis* Group B Outer Membrane Protein Produces Protective Antibodies against Gram-Negative Bacteremia," *The Journal of Infectious Diseases 173*:1157-1163, 1996.--.